(12) United States Patent
Kaufman et al.

(10) Patent No.: US 7,149,331 B1
(45) Date of Patent: Dec. 12, 2006

(54) METHODS AND SOFTWARE FOR IMPROVING THRESHOLDING OF CORONARY CALCIUM SCORING

(75) Inventors: Leon Kaufman, San Francisco, CA (US); Friederike Greiss, So. San Francisco, CA (US)

(73) Assignee: Cedara Software Corp., Ontario (CA)

(*) Notice: Subject to any disclaimer, the term of this patent is extended or adjusted under 35 U.S.C. 154(b) by 755 days.

(21) Appl. No.: 10/234,984

(22) Filed: Sep. 3, 2002

(51) Int. Cl.
*G06K 9/00* (2006.01)
(52) U.S. Cl. .................................... 382/128
(58) Field of Classification Search ............ None
See application file for complete search history.

(56) References Cited

U.S. PATENT DOCUMENTS

| | | | |
|---|---|---|---|
| 4,135,247 A | 1/1979 | Gordon et al. | |
| 4,613,754 A | 9/1986 | Vinegar et al. | |
| 4,974,598 A * | 12/1990 | John ........................ | 600/509 |
| 5,170,439 A | 12/1992 | Zeng et al. | |
| 5,325,293 A | 6/1994 | Dorne | |
| 5,335,260 A * | 8/1994 | Arnold ........................ | 378/207 |
| 5,396,886 A * | 3/1995 | Cuypers ..................... | 600/301 |
| 5,446,799 A | 8/1995 | Tuy | |
| 5,528,492 A | 6/1996 | Fukushima | |
| 5,549,117 A | 8/1996 | Tacklind et al. | |
| 5,570,404 A | 10/1996 | Liang et al. | |
| 5,581,460 A | 12/1996 | Kotake et al. | |
| 5,704,371 A | 1/1998 | Shepard | |
| 5,729,620 A | 3/1998 | Wang | |
| 5,768,406 A * | 6/1998 | Abdel-Mottaleb ......... | 382/132 |
| 5,807,256 A | 9/1998 | Taguchi et al. | |
| 5,832,450 A | 11/1998 | Myers et al. | |
| 5,832,504 A | 11/1998 | Tripathi et al. | |
| 5,895,461 A | 4/1999 | De La Huerga et al. | |
| 5,911,133 A | 6/1999 | Soble | |
| 5,950,207 A | 9/1999 | Mortimore et al. | |
| 5,986,662 A | 11/1999 | Argiro et al. | |
| 6,029,138 A | 2/2000 | Khorasani et al. | |
| 6,049,622 A | 4/2000 | Robb et al. | |
| 6,058,322 A * | 5/2000 | Nishikawa et al. ......... | 600/408 |
| 6,061,419 A | 5/2000 | Hsieh et al. | |
| 6,061,695 A | 5/2000 | Slivka et al. | |
| 6,083,162 A | 7/2000 | Vining | |
| 6,088,488 A | 7/2000 | Hardy et al. | |
| 6,110,109 A * | 8/2000 | Hu et al. ................... | 600/300 |
| 6,122,351 A | 9/2000 | Schlueter, Jr. et al. | |
| 6,133,918 A | 10/2000 | Conrad et al. | |
| 6,137,898 A * | 10/2000 | Broussard et al. ......... | 382/132 |
| 6,190,334 B1 | 2/2001 | Lasky et al. | |
| 6,205,871 B1 | 3/2001 | Saloner et al. | |
| 6,226,352 B1 | 5/2001 | Salb | |
| 6,233,304 B1 | 5/2001 | Hu et al. | |

(Continued)

OTHER PUBLICATIONS

"ADC Full Leg / Full Spine Software" Product Brochure by AGFA-Gevaert N.V. Belgium, B-2640 Mortsel-Belguim NE3JT GB 00200101, 2 pages total.

(Continued)

*Primary Examiner*—Samir Ahmed
*Assistant Examiner*—O'Neal R. Mistry
(74) *Attorney, Agent, or Firm*—Townsend and Townsend and Crew LLP

(57) ABSTRACT

The present invention provides methods and software for improving thresholding of coronary calcium scoring. In exemplary embodiments, the present invention applies an automatic search algorithm to slice images of an image scan to generate an individualized signal threshold for each particular patient. In other embodiments, an individualized signal threshold is generated for each slice image of the image scan.

58 Claims, 5 Drawing Sheets

U.S. PATENT DOCUMENTS

| | | | |
|---|---|---|---|
| 6,253,214 B1 | 6/2001 | Hall et al. | |
| 6,304,848 B1 | 10/2001 | Singer | |
| 6,317,617 B1 | 11/2001 | Gilhujis et al. | |
| 6,320,931 B1 | 11/2001 | Arnold | |
| 6,348,793 B1 | 2/2002 | Balloni et al. | |
| 6,366,638 B1 | 4/2002 | Hsieh et al. | |
| 6,430,430 B1* | 8/2002 | Gosche | 600/410 |
| 6,460,003 B1 | 10/2002 | Kump et al. | |
| 6,674,834 B1 | 1/2004 | Acharya et al. | |
| 6,674,880 B1 | 1/2004 | Stork et al. | |
| 6,697,415 B1 | 2/2004 | Mahany | |
| 6,813,393 B1 | 11/2004 | Takeo | |
| 6,928,182 B1 | 8/2005 | Chui | |
| 2001/0031076 A1* | 10/2001 | Campanini et al. | 382/128 |
| 2002/0081006 A1* | 6/2002 | Rogers et al. | 382/128 |
| 2002/0193687 A1* | 12/2002 | Vining et al. | 600/425 |
| 2003/0048867 A1 | 3/2003 | Kishore et al. | |
| 2003/0095693 A1* | 5/2003 | Kaufman et al. | 382/128 |
| 2003/0095695 A1* | 5/2003 | Arnold | 382/131 |
| 2003/0165262 A1* | 9/2003 | Nishikawa et al. | 382/128 |
| 2003/0176780 A1* | 9/2003 | Arnold et al. | 600/407 |
| 2003/0215124 A1* | 11/2003 | Li | 382/131 |
| 2004/0069951 A1 | 4/2004 | Jones et al. | |
| 2005/0281478 A1 | 12/2005 | Kaufman et al. | |

OTHER PUBLICATIONS

Agatston et al., "Quantification of Coronary Artery Calcium Using Ultrafast Computed Tomography," *JACC*, (Mar. 15, 1990) vol. 15, No. 4, pp. 827-832.

Brown et al., "Method for Segmenting Chest CT Image Data Using an Anatomical Model: Preliminary Results," *IEEE Transactions on Medical Imaging*, (Dec. 1997) vol. 16, No. 6, pp. 828-839.

Grundy, Scott M., MD, Ph.D., "Coronary Plaque as a Replacement for Age as a Risk Factor in Global Risk Assessment," *The American Journal of Cardiology*, (Jul. 19, 2001) vol. 88 (2A), pp. 8E-11E.

Hoff et al., "Age and Gender Distributions of Coronary Artery Calcium Detected by Electron Beam Tomography in 35,246 Adults," *The American Journal of Cardiology*, (Jun. 15, 2001) vol. 87, pp. 1335-1339.

Raggi et al., "Calcium Scoring of the Coronary Artery by Electron Beam CT: How to Apply an Individual Attenuation Threshold" (Feb. 2002) AJR vol. 178, pp. 497-502.

Rumberger et al., "Electron Beam Computed Tomographic Coronary Calcium Scanning: A Review and Guidelines for Use in Asymptomatic Persons," *Mayo Foundation for Medical Education and Research*, (Mar. 1999) vol. 74, pp. 243-252.

Schmermund et al., "An Algorithm for Noninvasive Identification of Angiographic Three-Vessel and/or Left Main Coronary Artery Disease in Symptomatic Patients on the Basis of Cardiac Risk and Electron-Beam Computed Tomographic Calcium Scores," *Journal of the American College of Cardiology*, (1999) vol. 33, No. 2, pp. 444-452.

Sutton-Tyrell et al., "Usefulness of Electron Beam Tomography to Detect Progression of Coronary and Aortic Calcium in Middle-Aged Women," *The American Journal of Cardiology*, (Mar. 1, 2001) vol. 87, pp. 560-564.

Zhu et al., "Accuracy of Area Measurements Made From MR Images Compared With Computed Tomography," *Journal of Computer Assisted Tomography* (Jan./Feb. 1986) vol. 10, No. 1, pp. 96-102.

U.S. Appl. No. 10/844,026, filed May 12, 2004, Kaufman.

U.S. Appl. No. 10/096,356, filed Mar. 11, 2002, Rumberger.

Acharya, K.C. et al., "Calcium score with electron beam and single slice helical CT: A three center study," Radiological Society of North America 86th Annual Meeting Abstract Book Suppl, 142:232-233 (2000).

Achenbach, S. et al., "Overlapping cross-sections significantly improve the reproducibility of coronary calcium measurements by electron beam tomography: A phantom study" *J. Comput. Assist. Tomogr.*, 25(4):569-573 (2001).

Agatston, A.S. et al., "Electron beam CT coronary calcium predicts future coronary events (abstr)," Abstract 2097, *Circulation*, 94:1/360 (1996).

Arad, Y. et al., "Predictive value of electron beam computed tomography of the coronary arteries: 19-month follow-up of 1173 asymptomatic subjects," *Circulation*, 93:1951-1953 (1996), printed from internet Aug. 17, 2004.

Baumgart, D. et al., "Comparison of electron beam computed tomography with intracoronary ultrasound and coronary angiography for detection of coronary atherosclerosis," *JACC*, 30(1):57-64 (1997).

Becker, C.R. et al., "Helical and single-slice conventional CT versus electron beam CT for the quantification of coronary artery calcification," *A.J.R.*, 174:543-547 (2000).

Bielak, L.F. et al., "Coronary artery calcification measured at electron-beam CT: Agreement in dual scan runs and change over time," *Radiology*, 218(1):224-229 (2001).

Boese, J.M. et al., "Optimizing temporal resolution in CT with retrospective ECG gating," *Radiologe*, 40(2):123-129 (2000). [in German].

Callister, T.Q. et al., "Coronary artery disease: Improved reproducibility of calcium scoring with an electron-beam CT volumetric method," *Radiology*, 208:807-814 (1998).

Carr, J.J. et al., "Evaluation of subsecond gated helical CT for quantification of coronary artery calcium and comparison with electron beam CT," *A.J.R.*, 174:915:921 (2000).

Detrano, R. (Hong) et al., "Prognostic value of coronary calcification and angiographic stenoses in patients undergoing coronary angiography," *JACC*, 27:285-290 (1996).

Georgiou, D. et al., "Screening patients with chest pain in the emergency department using electron beam tomography: A follow-up study," *JACC*, 38(1):105-110 (2001).

Goldin, J.G. et al., "Spiral versus electron-beam CT for coronary artery calcium scoring," *Radiology*, 221:213-221 (2001).

Hoffman, U. et al., "Precision and variability of multiple scoring methods for ex vivo quantification of vascular calcification by multidetector computed tomography," Abstract 30, *Radiology*, 225(P):240 (2002).

Hong, C. et al., "Coronary artery calcium: absolute quantification in nonenhanced and contrast-enhanced multi-detector row CT studies," *Radiology*, 223:474-480 (2002).

Hong, C. et al., "Coronary artery calcium: accuracy and reproducibility of measurements with multi-detector row CT—assessment of effects of different thresholds and quantification methods," *Radiology*, 227:795-801 (2003).

Kaufman et al., "Quantitative Characterization of Signal-to-Noise Ratios in Diagnostic Imaging Instrumentation," *Prog. Nucl. Med.*, 7:1-17 (1981).

Kaufman et al., "Methods for Evaluation of Diagnostic Imaging Instrumentation," *Phys. Med. Biol.*, 26(1):101-112 (1981).

Kaufman et al., "Generalized Methodology for the Comparison of diagnostic Imaging Instrumentation," AFIPS Press, 49:445-451 (1980).

Kaufman et al., "Measurement of the Texture Contribution to Image Noise in Scintigrams," Applications of Optical Instrumentation in Medicine VII, SPIE 233:134-136 (1980).

Lawler, L.P. et al., "Coronary artery calcification scoring by multidetector CT: Is it reliable and reproducible?" *Radiological Society of North America 86th Annual Meeting Abstract Book Suppl.*, p. 502, abstract # 1127 (2000).

Mao, S. et al., "Effect of electrocardiogram triggering on reproducibility of coronary artery calcium scoring," *Radiology*, 220:707-711 (2001).

Mao, S. et al., "Improved reproducibility of coronary artery calcium scoring by electron beam tomography with a new electrocardiographic trigger method," *Invest. Radiol.*, 36(7):363-367 (2001).

Möhlenkamp, S. et al., "Reproducibility of two coronary calcium quantification algorithms in patients with different degrees of calcification," *Int. J. Cardiovasc. Imaging*, 17:133-142 (2001).

Ohnesorge, B.M et al., "Cardiac imaging by means of electrocardiographically gated multisection spiral CT: Initial Experience," *Radiology*, 217:564-571 (2000).

Ohnesorge, B.M. et al., "Reproducibility of coronary calcium scoring with EBCT and ECG-gated multi-slice spiral CT," *Radiological Society of North America 86th Annual Meeting Abstract Book* abstract 143, p. 233, (2000).

Qanadli, S.D. et al., "Volumetric quantification of coronary artery calcifications using dual-slice spiral CT scanner: Improved reproducibility of measurements with 180° linear interpolation algorithm," *J. Comput. Assist. Tomogr.*, 25(2):278-286 (2001).

Raggi, P. et al., "Use of electron beam tomography data to develop models for prediction of hard coronary events," *American Heart J.*, 141(3):375-382 (2001).

Rumberger et al., "A rosetta stone for coronary calcium risk stratification: Agatston, volume and mass scores in 11,490 individuals," *AJR*, 181:743-748 (2003).

Secci, A. et al., "Electron Beam computed tomographic coronary calcium as a predictor of coronary events: Camparison of two protocols," *Circulation*, 96:1122-1129 (1997), printed from internet Aug. 17, 2004.

Stanford, W. et al., "Coronary artery calcium: Comaparison of electron beam CT with helical CT," *Radiological Society of North America 86th Annual Meeting Abstract Book*, abstract 1586, p. 589 (2000).

Takahashi, N. et al., "Coronary calcium scoring using multi-slice CT: Evaluation of interscan variability and optimal scan tube current," *Radiological Society of North America 86th Annual Meeting Abstract Book*, abstract 1126, p. 501 (2000).

Wexler, L. et al., "Coronary artery calcification: pathophysiology, epidemiology, image methods and clinical implications: A scientific statement for health professionals from the American Heart Association," Circulation 94:1175-1192 (1996), printed from internet Aug. 17, 2004.

Wilson et al., "Prediction of coronary heart disease using risk factor categories," *Circulation*, 97:1837-1847 (1998).

* cited by examiner

METHODS AND SOFTWARE FOR IMPROVING THRESHOLDING OF CORONARY CALCIUM SCORING

CROSS-REFERENCES TO RELATED APPLICATIONS

The present application is related to U.S. patent application Ser. No. 10/096,356, filed on Mar. 11, 2002 and U.S. patent application Ser. No. 10/126,463, filed Apr. 18, 2002, the complete disclosures of which are incorporated herein by reference.

BACKGROUND OF THE INVENTION

The present invention relates generally to coronary calcium scoring. More specifically, the present invention relates to methods, software, and systems that generate a patient-specific signal threshold for improving the sensitivity and accuracy of coronary calcium scoring, although the same method could be used in other applications such as contrast enhancement studies, time density analysis, and the like.

Coronary artery disease is a leading cause of death in the United States and other industrialized nations. Unfortunately, diagnosis of coronary artery disease is generally not made until the patient becomes symptomatic. By that time, the coronary artery disease may be advanced or the patient may have already had a myocardial infarction (i.e., heart attack).

One promising non-invasive method of detecting coronary artery disease in its early stage is "coronary calcium scoring," which can measure a level of the patient's coronary calcium in the patient's coronary arteries. Although the current orthodoxy is that the rupture of soft plaque and subsequent thrombus formation is the major precursor of acute coronary events, in most individuals it is believed that the coronary calcium measurement is also a valid surrogate or indicator of total plaque burden, including soft plaque.

Calcium scoring is quickly becoming a major focus in the effort to assess risk for coronary heart disease, to monitor progression of plaque development, and to potentially assess therapies and interventions designed to reduce mortality from coronary heart disease. (See Rumberger J. A. et al, "Electron Beam Computed Tomographic Coronary Calcium Scanning: A Review and Guidelines for Use in Asymptomatic Persons," Mayo Clinic Proc. 1999; 74:243–252 and Schmermund A., et al, "An Algorithm for Noninvasive Identification of Angiographic Three-Vessel and/or left Main Coronary Artery Disease in Symptomatic Patients," J. Am. Coll. Cardiology 1999; 33:444–452, the complete disclosure of which are incorporated herein by reference). While calcium scoring was initially concentrated in finding the 10–25% of the population with high calcium scores and at high risk for a short term coronary event, the focus is now shifting to finding early disease and to plan preventive treatments. Some forms of treatment are benign, such as diet and exercise, others include cholesterol-lowering drugs such as the statins, which are costly and have side effects. Early identification is becoming the frontier of coronary calcium scoring.

The assessment of risk from coronary calcium is generally a multi-step process: First, a patient is imaged, typically using a CT scanner. The multi-slice images are analyzed to identify the calcium and thereafter a calcium burden is quantitated by a "scoring" algorithm, most commonly with the Agatston scale. (See Agatston A. S. et al, "Quantification of Coronary Artery Calcium Using Ultrafast Computed Tomography," J. Am. Coll. Cardiology 1990; 15:827–832, the complete disclosure of which is incorporated herein by reference). Next, the measured calcium burden, age, gender of the individual, and other factors are used to rank the individual against his or her age-matched cohort to calculate the patient's risk for a coronary event.

While conventional calcium scoring methods are effective in estimating the amount of calcium in the patient's coronary arteries, improvements are still needed. For example, conventional coronary calcium scoring is generally performed using a fixed attenuation threshold (typically about 130 HU for EBCT and between 90 HU and 130 HU for CT) to allow for differentiating between calcium deposits and the surrounding soft-tissue.

Because the calcium scoring procedure has to be robust, this threshold is set high enough so that in the worst noise case, the score is reliable in that it represents a calcium deposit rather than noise fluctuations. Unfortunately, the high threshold also means that for most patients being studied and for most slices being evaluated, the threshold is set higher than necessary and true lesions may be missed (e.g., false negatives). On the other hand, if the signal threshold is set too low, noise or other artifacts may be thought to be lesions and "false positives" may be scored. Both false negatives and false positives are undesirable since both affect the accuracy of the patient's calcium score and consequent recommendations.

Because the fixed attenuation threshold does not compensate for noise differences in the specific image scanner being used (e.g. beam hardening artifacts, scanner imperfections, differences between scanner models, and the like) and variances of the tissue density for each patient, the fixed threshold is generally set high enough to prevent false-positive detections, e.g., high enough so that the noise in the image is not confused with the calcium deposits in almost all patients. Importantly, noise in the images may cause some or all of the early lesions to be missed. Since the early lesions are smaller in size and generate a weaker signal in the slice image, these weaker signals can be easily hidden by being above the noise levels, but below the attenuation threshold used to differentiate the "calcium" deposits from the noise and surrounding tissue.

One proposed alternative method to using a fixed threshold is described in Raggi et al., "Calcium Scoring of the Coronary Artery by Electron Beam CT: How to Apply an Individual Attenuation Threshold," A. J. R. Vol. 178, February 2002, pp. 497–502. Raggi et al. suggest the use of an individualized threshold setting instead of the fixed threshold of 130 HU for the Agatston and volume scores using an Electron Beam CT scanner. Raggi et al. describes setting the threshold at three standard deviations above the background level. From such calculations, Raggi et al. concludes that a threshold of 120 HU (which equals the background level plus three standard deviations) is more appropriate than the more common threshold of 130 HU.

The threshold calculated by Raggi et al. is expected to have a certain number of "false positives," (e.g., noise that is above the threshold) and for different values of the multiplier of the standard deviation, the false positives would vary in a predictable manner. Whatever the multiplier is, it is selected ahead of time for all slices in all patients.

Unfortunately, Raggi et al's proposed solution still has problems which makes it difficult to produce a reliable estimate of the false positives and use the highest sensitivity (i.e., lowest threshold) compatible with the number of false positives that are deemed acceptable. The major problem has to do with understanding what the standard deviation signifies. Raggi et al.'s expectation of three standard deviations to yield a certain number of false positives is not operational since the number of false positives will be different depending on the size of the lesion that is analyzed. Given the data analysis tools provided by a conventional CT scanner, it is difficult to know what level of false positives that will be generated for any one size lesion.

These considerations are based on the behavior of CT scanner noise (e.g., standard deviation). Scanner imperfections, such as bad detectors, small changes in detector behavior after calibration, bone and air in the subject, motion and reconstruction algorithms, all introduce noise that is not stochastic, i.e., its behavior is not predicted by statistics. Such noise is called structured noise. The frequency distribution of the structured noise will depend on the particulars of how it is being generated and is unpredictable. The effect of such noise will show up where it has repetition patterns (e.g., at its spatial frequency), so a calculation of a standard deviation for single pixels will not necessarily reflect the noise present in the image at the lesion sizes of interest. Because such structured noise is common in CT imaging, using a multiple of the standard deviation for setting thresholds does not provide a reliable provider of the false positive rate that will be achieved.

For the above reasons, what are needed are improved methods, software, and devices which improve coronary calcium scoring.

BRIEF SUMMARY OF THE INVENTION

The present invention provides methods, software, and systems for generating an individualized signal threshold for improving coronary calcium scoring. More particularly, the methods of the present invention can be used to create a slice-specific signal threshold for calcium scoring of each slice image of an image scan of a patient. By setting the threshold individually, on a patient by patient or on a slice-by-slice basis, the maximum sensitivity available from any one CT scanner becomes available for the detection of small lesions so that a more accurate coronary calcium score can be obtained.

The present invention can account for inter- and intraindividual variability of soft-tissue attenuation of the patient's slice images, the variability between different scanners, and stochastic and structured noise by individually analyzing each slice image to calculate the noise structure in each slice image.

In exemplary embodiments, the methods of the present invention use a lesion criteria to determine whether an area of interest (e.g., a grouping of pixels) is a calcium lesion or noise. The lesion criteria for selecting the signal threshold can be entered by the operator and the present invention can automatically analyze the slice images to generate an individualized signal threshold for the patient and/or individual slices. If desired, in some methods the operator can re-score a patient's calcium burden by applying different signal threshold criteria to see how the selection criteria affects the patient's calculated calcium burden. If desired, the operator can present all or some of the calcium scores to the patient.

In one aspect, the present invention provides a method of generating an individualized signal threshold for each slice image of an image scan. The method comprises selecting at least one region of interest in each of the plurality of slice images. A signal threshold for each of the plurality of slice images is generated by applying an automatic search algorithm to the selected region of interest in each of the slice images.

In exemplary embodiments, the region of interest on each of the slice images is chosen in a uniform or homogeneous area of the slice image that have substantially the same signal intensity under CT imaging. Such homogeneous regions may be near the coronary arteries and include, but are not limited to, muscle, a blood pool, the aorta, or the heart itself. The region of interest is typically an area of the patient's anatomy that cannot have calcium deposits. Thus, any groupings of pixels that meet the lesion criteria in the selected region of interest must by noise and are considered false positives.

The methods of the present invention inherently take into account the characteristics of the noise structure that is present in the slice images. Most prior art methods do not treat noise with care and provide less than optimal signal thresholds and coronary calcium scores.

Noise has two components. One component of the noise is stochastic noise that is caused by photon counting statistics. The stochastic noise will vary with CT scanner model used to image the patient, the operating conditions (e.g., dose delivery considerations), and with the size of the patient. The second component of noise is due to artifacts, which is structured noise. Sources of structured noise can be reconstruction algorithms, beam hardening artifacts, motion, scanner imperfections, and the like. Both components of noise will not only vary for the above parameters, but the noise will vary from slice-to-slice during the same image scan due to the differences in geometry and motion. By selecting a region of interest that cannot have calcium, the present invention individually analyzes the noise structure in each slice and provides improved signal thresholds and coronary calcium scores.

An operator can select the homogeneous area of the slice image by drawing a region-of-interest (ROI) directly on the slice image. The region of interest can be selected using conventional methods, such as pointing a cursor and dragging the mouse to create the region of interest.

The automatic search algorithms of the present invention can be used to generate an individualized threshold for the slice image by analyzing the region of interest. The search algorithm can analyze a variety of factors in the region of interest to generate the signal threshold for the slice image. In one exemplary embodiment, the automatic search algorithm uses an operator-selected lesion criteria to analyze the region of interest to generate the signal threshold for the slice image.

In another aspect, the present invention provides a method of using an operator-selected lesion criteria to generate an individualized signal threshold for the individual slice images of an image scan. The method comprises applying the lesion criteria for locating false positives in a region of interest in each slice image. The lesion criteria defines an operator defined acceptable number of false positives N. The slice image is computer processed according to the lesion criteria to generate the individualized signal threshold for each slice image.

In exemplary embodiments, the lesion criteria for determining whether an area of interest is a calcium lesion or noise includes at least one of a minimum area, a minimum connectedness, and/or an acceptable number of false positives. In some embodiments, the operator can be prompted to enter all of the selection criteria. In other embodiments, however, some of the criteria may be pre-set and the operator need only select some of the criteria. It should be appreciated however, that the lesion criteria may include other criteria, such as connection across slices, not just in plane.

Once the operator has selected the lesion criteria, the methods of the present invention can automatically select and adjust a signal threshold to locate groupings of pixels that exceed the signal threshold and have the minimum connectedness and area. In a specific configuration, the methods of the present invention will apply a first, pre-selected signal threshold, minimum connectedness and minimum area lesion criteria and locate any groupings of pixels that meet the criteria. The number of "false positives" located with the criteria can then be automatically counted. If the number of false positives exceed (or are equal to or less than) the pre-selected "acceptable number of false positives," the first signal threshold is deemed to be unacceptable and the first signal threshold is adjusted upwards (or downwards) until the acceptable number of false positives is found. The acceptable number of false positives can be an absolute number (zero or an integer) or a percent probability that a lesion is false. Once a signal threshold is found that locates the acceptable number of false positive, that signal threshold (or a signal threshold close to it) can be set as the signal threshold for that slice image. The process can be repeated for each slice image so as to generate an individualized image threshold for each slice image.

In yet another aspect, the present invention provides a method for improving coronary calcium scoring of an image scan that has a plurality of slice images. The method comprises applying an automatic search algorithm to each slice image to calculate an individualized signal threshold for each slice image. The individualized signal threshold can be applied to each of their respective slice images so as to identify calcium in each slice image.

In exemplary embodiments, the automatic search algorithms of the present invention use objective criteria to automatically locate false lesions in the slice images, compare the located number of false lesions with the operator defined "acceptable number of false lesions," and adjust the signal threshold until the acceptable number of false lesions is found. The automatic analysis of all of the slices can be run according to a predetermined program to improve efficiency of the operator and generate a more accurate, individualized signal threshold for the patient.

Once the individualized threshold for each slice is found, the individualized thresholds can be used to analyze each of the slice images to identify calcium in the coronary arteries. In other embodiments, however, the operator (or the computer software) can select one "universal" signal threshold to calcium score all of the slice images. In either case, the identified calcium located in each of the slice images can then be analyzed to calculate an Agatston Score and/or a calcium volume score.

The methods of the present invention can be embodied in a software algorithm, a computer readable medium (e.g., a hard drive, a CD-ROM, a floppy disk, CD-R, CD-RW, etc,), a computer system, an imaging system (e.g., CT scanner), and the like.

These and other aspects will be apparent from the following figures, description, and claims.

DETAILED DESCRIPTION OF THE INVENTION

The present invention provides methods for setting an individualized signal threshold for identifying calcium on a patient-by-patient, and more specifically on a slice-by-slice basis. Advantageously, the criteria used in setting the threshold may be controlled by the operator and the generation of the individualized threshold is automatically calculated by algorithms of the present invention.

After an image scan of a patient is obtained by a CT scanner (e.g., mechanical CT scanner, electron beam CT scanner, or a helical CT scanner), an operator can use the methods of the present invention to examine each of the slice images of the image scan to identify calcium for scoring.

Figure 1:
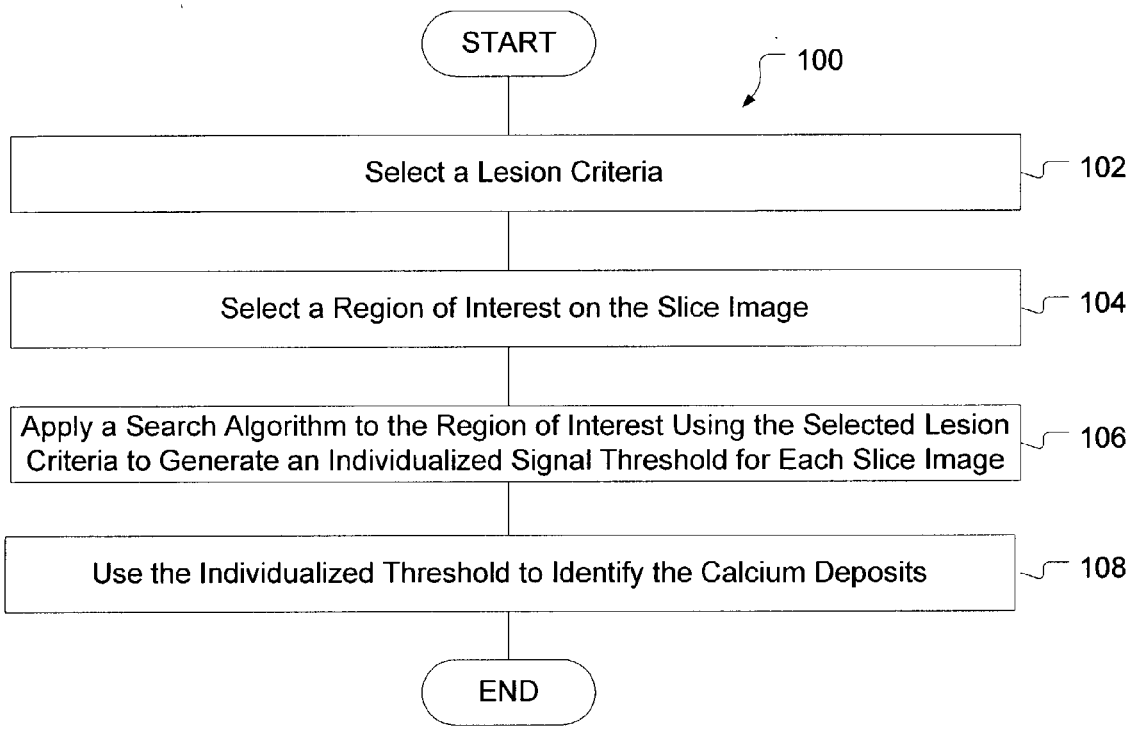
FIG. 1 is a simplified flow chart that schematically illustrates an exemplary method of the present invention.

FIG. 1 schematically illustrates a simplified method 100 of the present invention of generating an individualized signal threshold for identifying calcium deposits. The steps of the present invention are typically embodied in software that is run on a computer system. Some exemplary computer systems are described in commonly owned and copending U.S. patent application Ser. No. 10/096,356, filed on Mar. 11, 2002 and Ser. No. 10/126,463, filed Apr. 18, 2002, the complete disclosures of which are incorporated herein by reference. The software can be stored as code on a computer readable medium such as a floppy disk, hard drive, CD-ROM, CD-R, CD-RW, or the like.

Some exemplary methods of the present invention include selecting a lesion criteria. (Step 102). A region of interest (ROI) is selected on one or more slice images. (Step 104). In most embodiments, the operator can select a region of interest in each of the slice images. In other embodiments, however, the operator may only select a region of interest in selected slice images or the region of interest may be automatically selected by a selection algorithm running on the computer system. After the lesion criteria and region of interest are selected, a search algorithm is applied to generate an individualized signal threshold for each of the slice images that had a region of interest selected. (Step 106). After the thresholds are calculated, the individualized threshold can be applied to the slice images to identify calcium deposits in the patient's coronary arteries. (Step 108).

Figure 2:
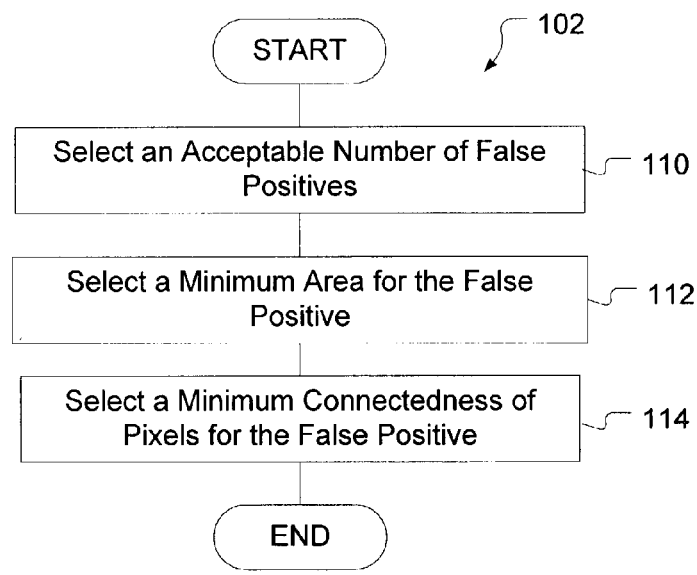
FIG. 2 is a simplified flow chart that schematically illustrates a lesion criteria of the present invention.

FIG. 2 illustrates one exemplary method 102 of selecting the lesion criteria. The lesion criteria of the present invention typically includes a plurality of operator-defined inputs. Software which runs the methods of the present invention, can be configured to prompt the operator to enter some or all of the inputs prior to analyzing the slice image. In alternative embodiments, the software can store the operator's preferences so that the operator does not have to enter the preferences for each image scan and the software can automatically apply the stored criteria to the slice images of the current image scan. As is illustrated in FIG. 2, the operator can be prompted to select at least one of an acceptable number of false positives 110, a minimum area for the false positives 112, and/or a minimum connectedness of the pixels for the false positives 114.

The acceptable number of false positives 110 can be selected as either 0, 1, 2, 3, 4 . . . or other integers. Alternatively, the operator can select the acceptable number of false positives as a percent probability p that a lesion is false. If the area of the region of interest and the area/connectedness criteria are known, it is possible to calculate how many individual potential lesions the region of interest can contain. For example, if the operator requests a 0.5% probability for false lesions, the computer will calculate the number of acceptable false lesions N as the closest integer to: (The total possible lesions in ROI)*(0.5)/100).

The minimum area for the false positives 112 can be defined as an area in $mm^2$ or by the number of pixels. In exemplary embodiments, the minimum area will be approximately 1 $mm^2$ or between approximately one and four pixels. It should be appreciated however, that the minimum area can be set by the operator to whatever level they desire. A higher minimum area will likely reduce the number of false positives located, while a lower the minimum area will likely cause more false positives to be located. This choice effects a tradeoff between sensitivity and specificity. The lower minimum area criteria are more sensitive to the presence of small lesions, but they are also more prone to characterizing noise as a lesion.

The minimum connectedness criteria 114 allows the operator to select the minimum number of pixels that are connected. The user may have the ability to select if the connectedness has to be side-by-side connection or corner-to-corner connection. These criteria also provide tradeoffs between sensitivity and specificity, with less stringent criteria (sides or corners) leading to higher sensitivity and lower sensitivity. Before or after the operator has selected their desired lesion criteria, the operator may be prompted to select a region of interest in one or more of the slice images. Typically, the software of the present invention will prompt the operator to select a region of interest in each of the slice images. In alternative methods, however, the operator may only desire to select less than all of the slices of the image scan. In other embodiments, however, the software of the present invention may incorporate an algorithm that automatically locates a desirable region of interest in each of the slice images by searching for areas of a given size and compactness that have the smallest standard deviation of the pixel values in that area.

Figure 3:
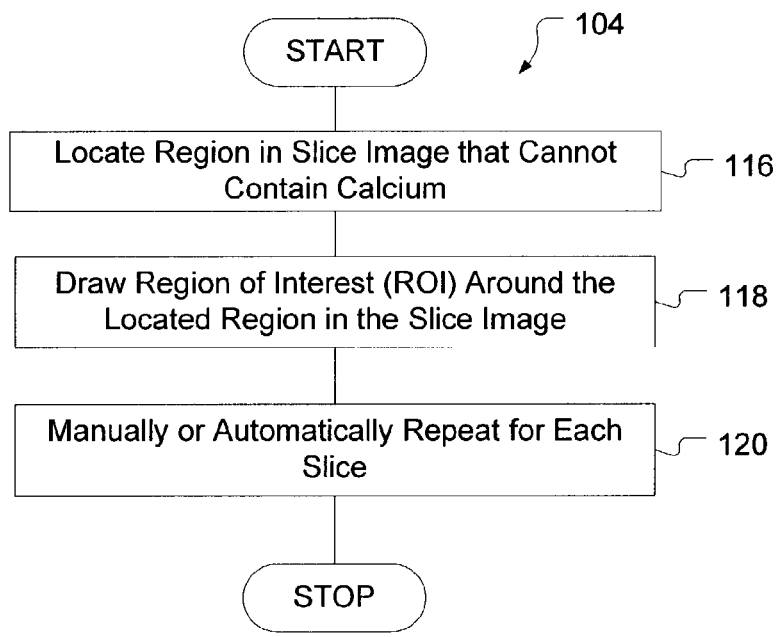
FIG. 3 is a simplified flow chart that schematically illustrates a method of selecting a region of interest in a slice image.

As shown in FIG. 3, to select the region of interest 104, the operator preferably locates a homogenous region of the slice image that cannot contain deposits. (Step 116). By selecting the region of interest in an area that cannot have calcium deposits, the methods of the present invention inherently take into account the characteristics of the noise structure (both stochastic and structured noise) in that any "lesions" found in the region of interest by the algorithm of the present invention must be noise. The homogeneous areas include, but are not limited to, the heart, the blood pool, the aorta, or the like.

To select the region of interest, the operator can draw the region of interest around the located region in the slice image. (Step 118). The region of interest can be drawn by activating an input device (such as a mouse, keyboard, joystick, a touchscreen, or the like) so as to position a cursor over the desired area of the slice image. In one exemplary embodiment, the region of interest can be created by holding down a button on the mouse and dragging the cursor over the desired region of interest. As can be appreciated, the region of interest can be created using a variety of other conventional methods. Once the operator has selected the region of interest in the slice image, the operator can manually repeat the selection of the region of interest for other image slices. (Step 120).

It should be appreciated, however, that in some embodiments, the software may be configured to automatically select a homogeneous region of interest in the other slice images for the operator. In such embodiments, if desired, the operator can then proceed through the slice images and amend the automatic selection of the region of interest. For this purpose, an algorithm that searches for areas of a given size and compactness that have the smallest standard deviation of the pixel values in that area can use the initially marked slice as a seed to limit its search area.

Figure 4:
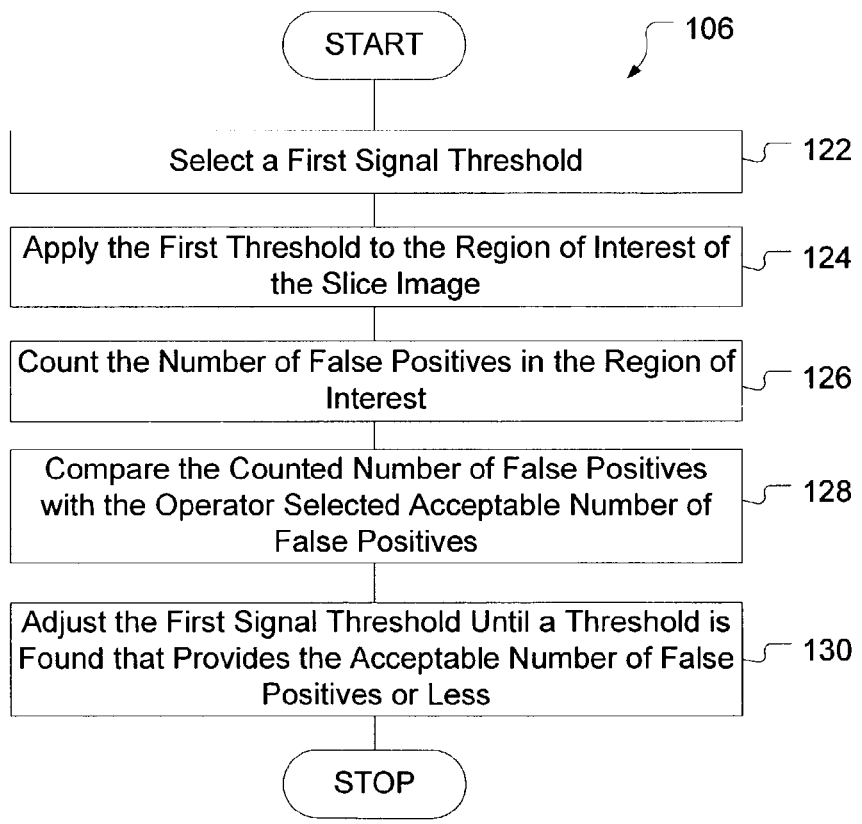
FIG. 4 is a simplified flow chart that schematically illustrates steps that can be performed by an automatic search algorithm of the present invention.

Once the lesion criteria 102 and the region of interest(s) 104 are selected, the operator can activate the software to apply the search algorithm to the slice images 106. FIG. 4 illustrates one simplified method 106 of how the search algorithm is applied to automatically generate an individualized signal threshold for the slice images.

The algorithm can select a low, first signal threshold $HU_1$. (Step 122). The first signal threshold can be preset by the manufacturers of the software or selected by the operator. The first signal threshold can be any desired HU level, but will typically be between 0 HU and 50 HU. It should be appreciated, however, that a too low first threshold may result in all pixels being above background and counting a single lesion which encompasses the a majority or the entire region of interest. This situation can be tested for by analyzing the size of the lesion relative to the size of the region of interest. In another approach to determining the initial threshold, the initial threshold is set at the mean of the HU values in the region of interest plus one standard deviation, and the number of lesions is computed with this threshold. If the total area of the lesions is bigger than a certain percentage (e.g., 25%) of the total area of the region of interest, one additional standard deviation can be added to the threshold. This process can be repeated until the area of the lesion(s) is smaller than the given percentage.

The first signal threshold $HU_1$ can be applied to filter out all pixels groupings that are not above the first signal threshold and do not meet the operator-defined lesion criteria (e.g., minimum area and minimum connectedness). (Step 124). Any pixel groupings that are not filtered out are considered "false positives." The number of false positives are counted. (Step 126). The number of counted false positives are compared with the operator defined acceptable number of false positives. (Step 128). If the counted number of false positives exceeds the acceptable number of false positives, the counting may stop and the first signal threshold $HU_1$ is adjusted until a signal threshold is found that provides the acceptable number of false positives (or less). (Step 130).

Figure 5:
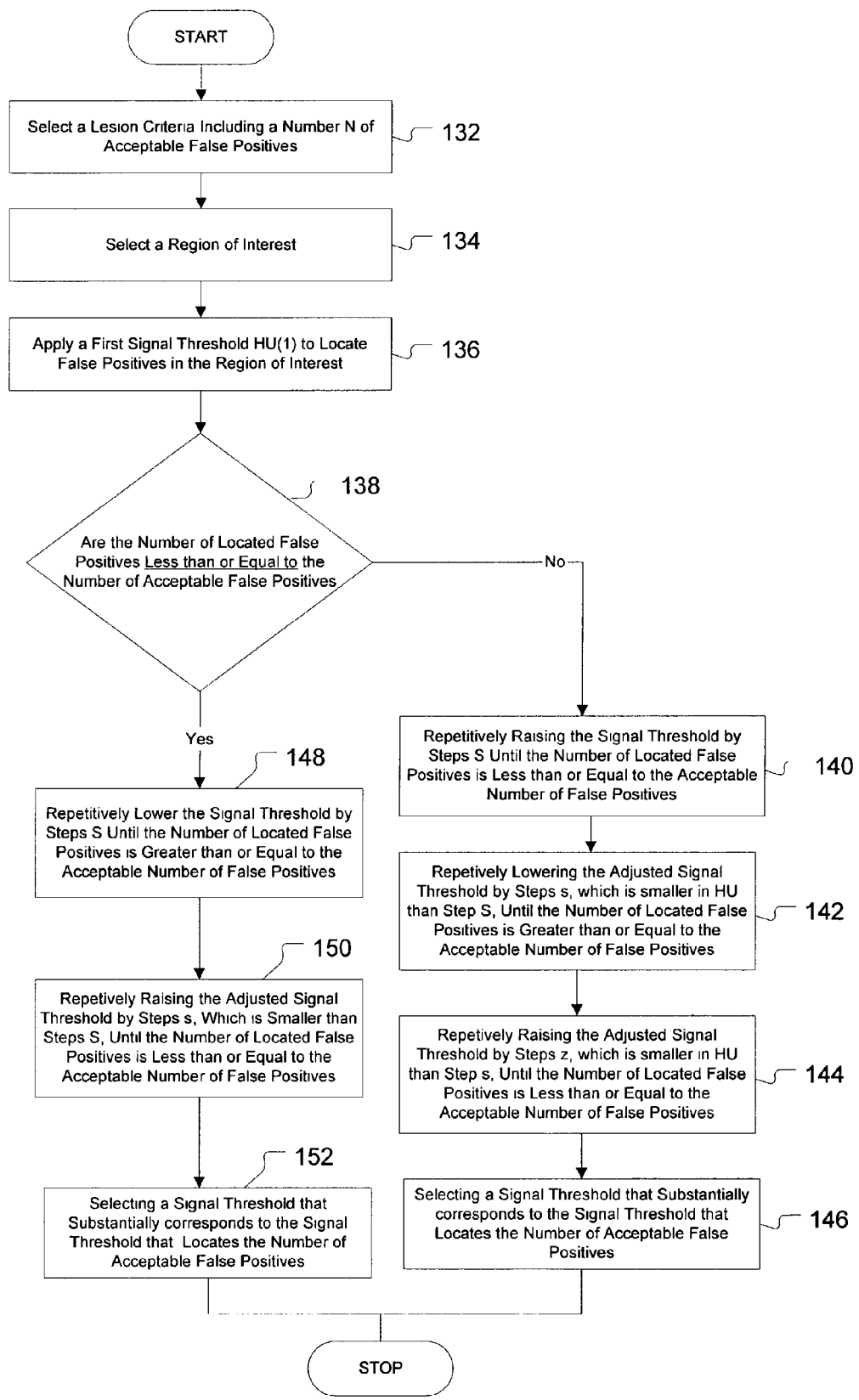
FIG. 5 is a simplified flow chart that schematically illustrates a detailed flow of information that can be performed by an automatic search algorithm of the present invention.
Figure 6:
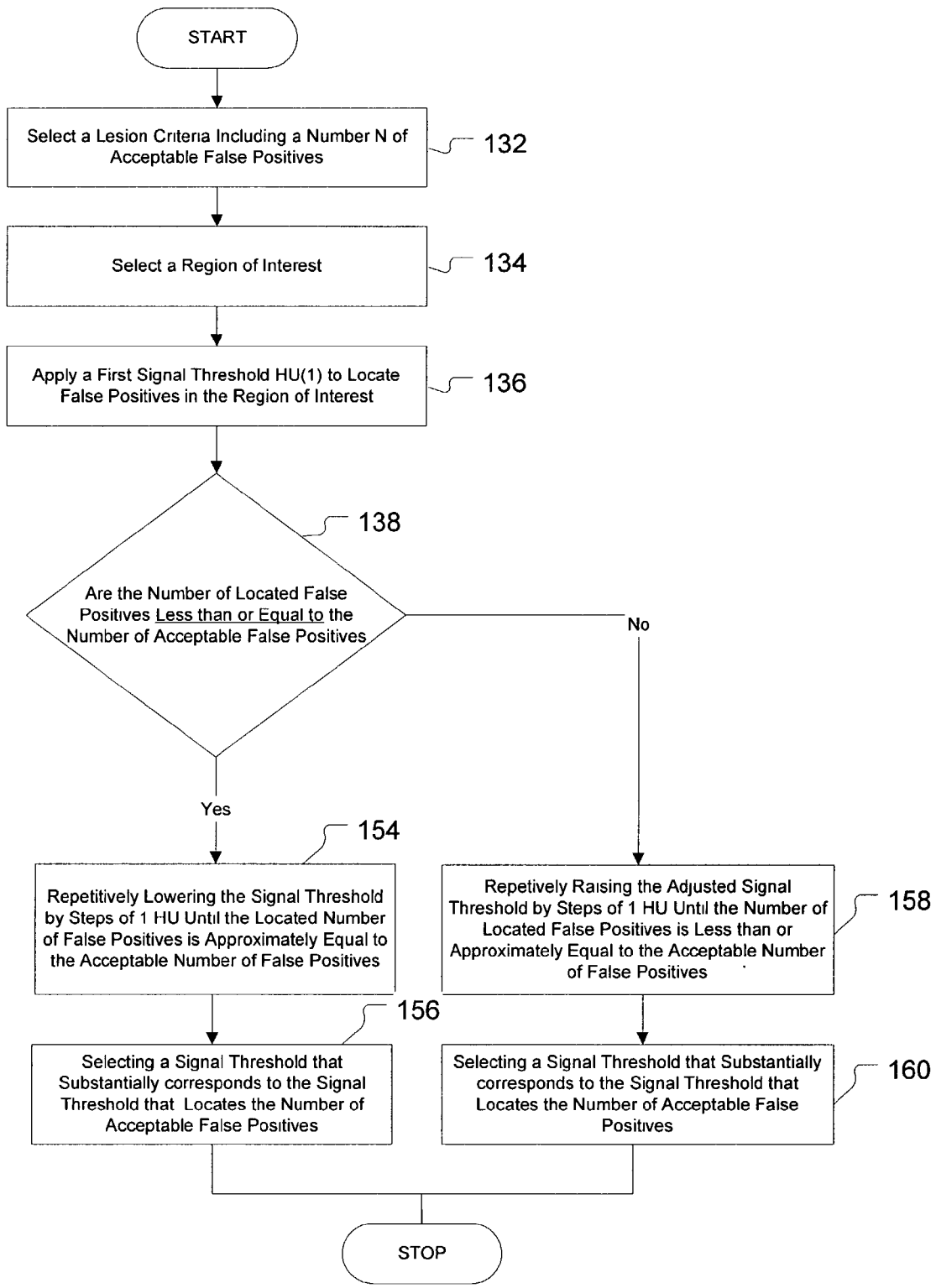
FIG. 6 is a simplified flow chart that schematically illustrates a detailed flow of information through an alternative automatic search algorithm of the present invention.

FIGS. 5–6 illustrate some more detailed methods of generating the individualized signal threshold. Generally, the illustrated methods may be carried out in the software through use of a predetermined program (either user selected or preset) so as to adjust the signal threshold through any combination of raising and lowering a first signal threshold $HU_1$ in order to find a signal threshold that provides the acceptable number of false positives.

As illustrated in FIG. 5 and described above, a lesion criteria is selected which includes an acceptable number of false positives N. (Step 132). A region of interest can be selected and a first signal threshold $HU_1$ is applied to the region of interest to locate false positives in the region of interest. (Steps 134 and 136). The number of false positives located in the region of interest is counted and compared to the acceptable number of false positives N. (Step 138). As soon as the number of counted false positives exceeds N, the counting can stop and the first threshold $HU_1$ will be raised, by a Step "S." The counting of false lesions is repeated, and the threshold is raised until the number of false positives located within the region of interest becomes N or smaller. (Step 140). At such point an adjusted signal threshold, $HU_2$ (e.g., the first threshold $HU_1$+(X number of raises)*"S" HU) can be temporarily saved in memory. Thereafter, the adjusted signal threshold $HU_2$ can be repetitively lowered by Steps "s," which is smaller in HU than Step "S," until the number of located false positives is equal to or greater than the acceptable number of false positives N. (Step 142). Again, an adjusted signal threshold $HU_3$, (e.g., $HU_2$+(Y number of raises)*"s" HU) can also be temporarily saved in memory. The signal threshold $HU_3$ can then be repetitively raised by steps "z," which is less than Steps "s," until a signal threshold $HU_F$ is found that locates a number of located false positives that is lower than or equal to the acceptable number of false positives N. (Step 144).

The final signal threshold $HU_F$ for the slice image can be selected to the HU value that substantially locates the acceptable number of false positives N. (Step 146). In exemplary embodiments, the final signal threshold $HU_F$ is a signal threshold that is one "z" HU or 1 HU step before where N was exceeded. In other embodiments, however, $HU_F$ can be set at the signal threshold at the point where N was exceeded. Such small differences in signal threshold (e.g., approximately 1 HU) will likely not affect the accuracy of the calcium scoring to a large extent.

At step 138, if the number of located false positives is less than the number of acceptable false positives N, then the first signal threshold $HU_1$ can be repetitively lowered by Steps "S" until the number of located false positives is greater than or equal to the acceptable number of false positives. (Step 148). The adjusted signal threshold $HU_2$ that corresponds to the number of false positives that is greater than or equal to the acceptable number of false positives can be temporarily stored in memory. Thereafter, the adjusted signal threshold $HU_2$ can be repetitively raised by steps "s," which is smaller than Step "S," until a signal threshold $HU_F$ is found that locates the number of located false positives that is lower than or equal to the acceptable number of false positives N. (Step 150). The final signal threshold $HU_F$ for the slice image can be selected to the HU value that substantially locates the acceptable number of false positives N. (Step 152). In one embodiment, $HU_F$ can be a "s" HU or 1 HU below the point where N was exceeded.

The HU levels of the initial signal threshold level $HU_1$ and Step S, Step s, and Step z will vary depending on operator preferences. The larger the HU steps are, the program will test the region of interest less number of times. As noted above, in exemplary embodiments, Step S is larger than Step s, and Step is larger than Step z.

In some embodiments, the initial signal threshold level $HU_J$ will typically be between 0 HU and 50 HU. Step S is typically between approximately 25 HU and 50 HU; step s is typically between approximately 10 HU and 25 HU; and step z is typically between 1 HU and 5 HU.

It should be appreciated, however, that the levels of the steps aren't critical and any operator desired HU level for each of the steps can be used. Moreover, additional steps or less steps can be used to find the desired signal threshold. For example, as is illustrated in FIG. 6, instead of using a plurality of different sized steps, the methods and predetermined programs of the present invention can merely raise or lower the signal threshold from the very start of the process by steps of 1 HU until the desired number of false positives are found.

Similar to the method illustrated in FIG. 5, a lesion criteria is selected which includes an acceptable number of false positives N. (Step 132). A region of interest can be selected and a first signal threshold $HU_1$ is applied to the region of interest to locate false positives in the region of interest. (Steps 134 and 136).

The number of false positives located in the region of interest is compared to the acceptable number of false positives N. (Step 138). If the number of located false positives is less than the number of acceptable false positives, then the first signal threshold $HU_1$ is repetitively lowered by steps of 1 HU until a signal threshold $HU_F$ is found that locates a number of false positives that is approximately equal to the operator-defined acceptable number of false positives N. (Step 154). Thereafter, the signal threshold for the slice image is selected that substantially corresponds to the signal threshold $HU_F$ that locates the number of acceptable of false positives N. (Step 156).

At step 138, if the number of located false positives is more than the acceptable number of false positives N, then the first signal threshold $HU_1$ is repetitively raised by Steps of 1 HU until a signal threshold $HU_F$ is found that locates a number of false positives in the region of interest that is approximately equal to the operator-defined acceptable number of false positives N. (Step 158). Thereafter, the signal threshold for the slice image is selected that substantially corresponds to the signal threshold $HU_F$ that locates the number of acceptable of false positives N. (Step 160).

It should be appreciated, that in other embodiments, instead of repetitively raising or lowering the signal threshold by steps of 1 HU, the signal threshold can be adjusted by steps that are larger (e.g., 2 HU, 5 HU, 10 HU).

Once the signal thresholds are generated for each of slice images using the above methods, the signal thresholds can be applied to each of the slices to identify calcium deposits in the coronary arteries. (FIG. 1, Step 108). Because each slice is analyzed using an individualized signal threshold, the early, small calcium deposits can be located, which can produce a more accurate scoring of the patient's overall calcium burden. Thereafter, using conventional methods the operator can calculate the patient's Agatston score and/or calcium volume score. If desired, the operator can generate a coronary calcium report for the patient. A description of an exemplary coronary calcium report is described in commonly owned and co-pending U.S. patent application Ser. No. 10/096,356, filed Mar. 11, 2002, the complete disclosure of which is incorporated herein by reference for all purposes.

Optionally, instead of applying an individualized signal threshold to each slice image, the operator can choose one of the slices to calculate a signal threshold that is to be applied to all the slices in the image set. For example, depending on the operator's preference, the operator may choose the highest (cephalad), the lowest (caudad), or middle slices, or any other slice threshold desired.

Figure 7:
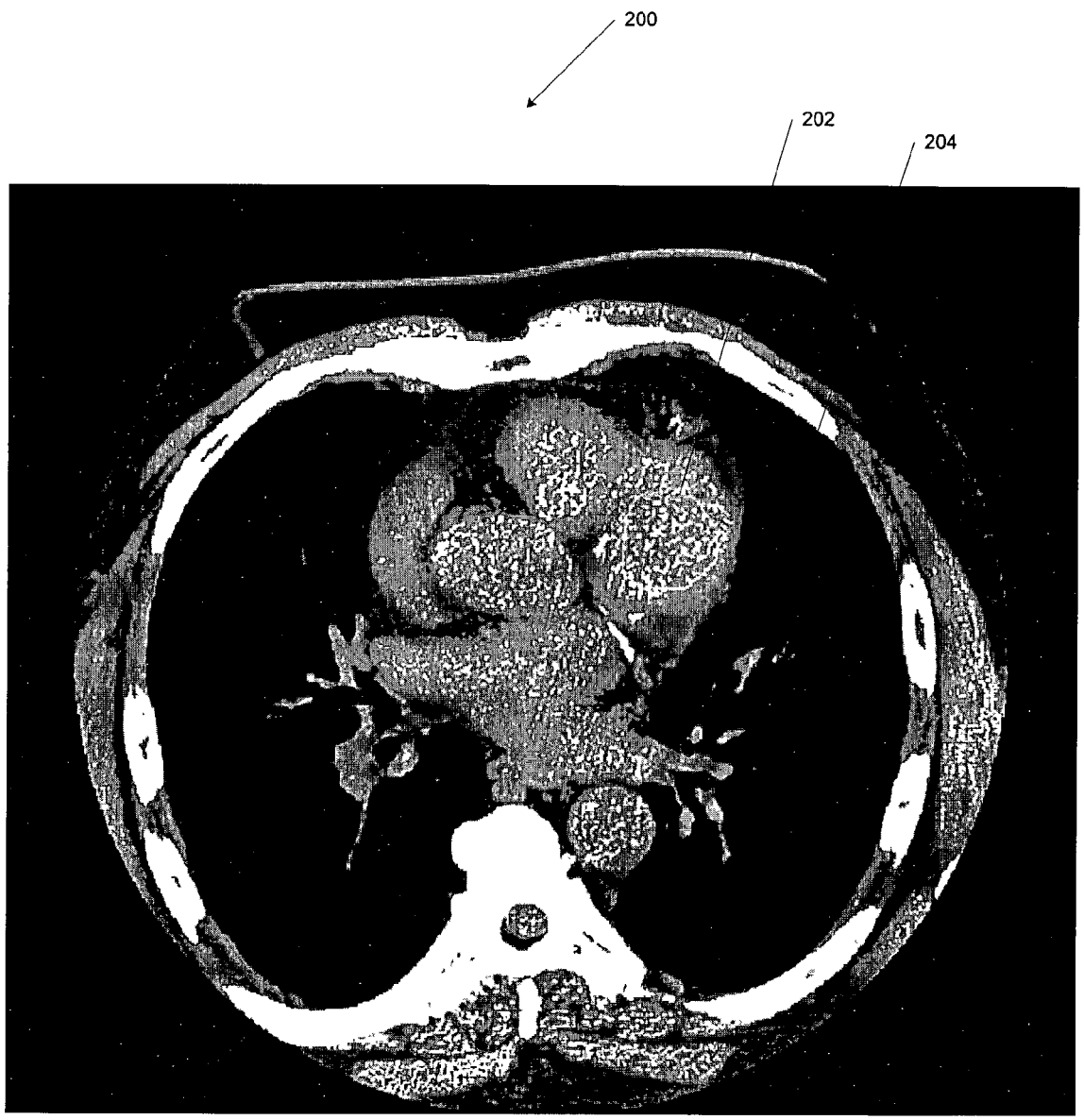
FIG. 7 shows a sample CT cross-section through the heart.

FIG. 7 shows a sample CT slice image 200. The slice image has a region of interest 202 drawn around a region that should not contain calcium. The light colored pixels are those above threshold, and include bone. All light colored pixels inside the region of interest are false positives. Just below this area can be a linear feature 204 in the 5 o'clock orientation, with two smaller regions above it. These are calcium deposits in coronary vessels.

It should be appreciated that while the above description is specific to calculating an individualized signal threshold for calcium scoring, the present invention is applicable to diagnosing other diseases. For example, the present invention is applicable to contrast media studies, time density analysis, bone mass estimations, and the like While the above is a complete description of the preferred embodiments, it should be appreciated that the above description should be regarded in an illustrative sense, rather than a restrictive sense. Additions, subtraction and other modifications can be made to the above examples without departing from the broad scope of the invention as set forth in the following claims. For example, a random search could be effected to find the desired level of false positives to any desired precision, e.g., 1 HU, 3 HU, etc.

What is claimed is:

1. A method for improving coronary calcium scoring of an image scan comprising a plurality of slice images, the method comprising:
    applying an automatic search algorithm to at least one slice image to calculate an individualized signal threshold for the at least one slice image;
    applying the individualized signal threshold to the at least one slice image to identify calcium therein; and
    selecting a region of interest in the at least one slice image in one or more areas that cannot have calcium, wherein the automatic search algorithm is applied to the region of interest to calculate the individualized signal threshold for the at least one slice image,
    wherein applying the automatic search algorithm comprises:
        selecting a lesion criteria, the lesion criteria comprising an acceptable number N of false positives that can be located in the region of interest;
        applying a first signal threshold $HU_1$ to the region of interest to locate false positives that have signal higher than the first signal threshold $HU_1$;
        counting the number of false positives located in the region of interest with the first signal threshold $HU_1$;
        comparing N with the number of false positives located in the region of interest with the first signal threshold $HU_1$; and
        adjusting the first signal threshold $HU_1$ until the number of false positives in the region of interest is less than or equal to N, wherein the individualized signal threshold for the at least one slice image is set substantially close to an adjusted signal threshold HU in which the number of false positives is less than or equal to N.

2. The method of claim 1 wherein the false positives comprise a grouping of pixels that have a minimum area, a minimum signal, and a minimum connectedness.

3. The method of claim 1 wherein the lesion criteria further comprises at least one of a minimum connectedness and/or a minimum area of pixels.

4. The method of claim 3 wherein selecting the lesion criteria comprises prompting an operator to provide at least one of the minimum connectedness, the minimum area of pixels, and/or a value representative of N.

5. The method of claim 4 wherein prompting the operator comprises having an operator provide each of the minimum connectedness, the minimum area of pixels, and the value representative of N before applying the automatic search algorithm.

6. The method of claim 3 wherein the minimum area of pixels is approximately 1 $mm^2$.

7. The method of claim 3 wherein the minimum connectedness comprises between approximately 1 pixel and 8 pixels.

8. The method of claim 1 wherein the value of N comprises zero or an integer.

9. The method of claim 1 wherein the value of N is a percent probability that a lesion is false.

10. The method of claim 1 wherein the first signal threshold $HU_1$ is between approximately 0 HU and 50 HU.

11. The method of claim 1 wherein adjusting the first signal threshold $HU_1$ comprises performing at least one of raising or lowering the signal threshold according to a predetermined program.

12. The method of claim 11 wherein the predetermined program comprises:
    repetitively raising the first signal threshold $HU_1$ a first step until the number of located false positives becomes N or smaller;
    repetitively lowering the raised first signal threshold a second step that is smaller than the first step until the number of located false positives exceeds N; and
    repetitively raising the signal threshold by a third step that is smaller than the second step until the number of located false positives becomes N or smaller.

13. The method of claim 12 wherein the first step is greater than the second step, and the second step is greater than the third step.

14. The method of claim 12 wherein the first step is between approximately 10 HU and 50 HU, the second step is between approximately 5 HU and 15 HU, and the third step is approximately 1 HU and 5 HU.

15. The method of claim 12 wherein the first step is between 10 and 50 HU.

16. The method of claim 12 wherein the first step is between 1 and 10 HU.

17. The method of claim 12 wherein the predetermined program further comprises setting the signal threshold for the at least one slice image after a predetermined number n of steps,
    wherein the signal threshold is selected as a HU value where one step increase of value n changes the number of false positives from a value larger than N, to N.

18. The method of claim 17 wherein the step n equals 1 HU.

19. The method of claim 17 where the step n equals 5 HU.

20. The method of claim 1 wherein adjusting the first signal threshold $HU_1$ comprises repeatedly raising or lowering the signal threshold by steps of 1 HU.

21. The method of claim 1 wherein adjusting the first signal threshold $HU_1$ comprises repeatedly raising or lowering the signal threshold by steps of 5 HU or less.

22. The method of claim 1 wherein if the first threshold $HU_1$ results in N false positives or less, then adjusting the first signal threshold comprises:
    reducing the first signal threshold $HU_1$ by a first step until the number of false positives exceeds N; and
    increasing the reduced first signal threshold $HU_1$ by a second step until the number of false positives is less than or equal to N,
    wherein the first step is greater than the second step.

23. The method of claim 1 wherein adjusting the first signal threshold $HU_1$ comprises raising the first signal threshold by steps of 1 HU until N false positives are found.

24. The method of claim 1 wherein the region of interest that cannot have calcium comprises a blood pool, an aorta, or a heart muscle.

25. The method of claim 1 wherein the at least one slice image is obtained with a mechanical CT scanner, an electron beam CT scanner, or a helical CT scanner.

26. The method of claim 1 comprising using the identified amount of calcium from the at least one slice image to calculate a patient's calcium volume.

27. The method of claim 1 comprising using the identified amount of calcium from the at least one slice image to calculate a patient's Agatston score.

28. The method of claim 1 comprising calculating a mean HU and a standard deviation of the region of interest, wherein the first signal threshold $HU_1$ is equal to approximately the mean HU plus one standard deviation.

29. The method of claim 1 wherein applying the first signal threshold $HU_1$ comprises analyzing a size of a lesion relative to a size of the region of interest, wherein if the size of the lesion is larger than a predetermined percentage, then the signal threshold is increased.

30. A method of generating an individualized signal threshold for each slice image of an image scan, the method comprising:
selecting at least one region of interest in each of the plurality of slice images;
generating a signal threshold for each of the plurality of slice images by applying an automatic search algorithm to the selected region of interest in each of the slice images comprising steps of:
applying a first signal threshold $HU_1$ to the first region of interest; counting the number of false positives located in the region of interest that are located with the first signal threshold $HU_1$; comparing the number of counted false positives with the value of N; and performing at least one of lowering or raising the first signal threshold $HU_1$ until a signal threshold is found that generates N false positives or lower, wherein the individualized signal threshold for the slice image is et substantially closes to an adjusted signal threshold in with N false positives are found; and
selecting lesion criteria, wherein the lesion criteria comprises a minimum area of the lesion, a minimum connectedness of the lesion, and a number N of acceptable false positives in the region of interest, wherein the signal threshold is generated based on the lesion criteria.

31. The method of claim 30 wherein the region or interest is operator selected, wherein the region of interest is an area of the slice image that does not contain calcium.

32. The method of claim 31 wherein the region of interest is a blood pool, an aorta, or a heart muscle.

33. The method of claim 30 wherein the image slices are obtained with a mechanical CT scanner, an electron beam CT scanner, or a helical CT scanner.

34. The method of claim 30 comprising using the identified amount of calcium from each slice image to calculate a patient's calcium volume.

35. The method of claim 30 comprising using the identified amount of calcium from each slice image to calculate a patient's Agatston score.

36. A method of using an operator-defined lesion criteria to generate an individualized signal threshold for individual slice images of an image scan, the method comprising:
selecting the lesion criteria for locating false positives in a region of interest in each slice image, wherein the lesion criteria includes an operator-provided acceptable number of false positives, represented by N; and
computer processing the slice image according to the lesion criteria to generate the individualized signal threshold for each slice images,
wherein the region of interest is examined with a first threshold and a number of false positives that meet the criteria of calcium lesions is counted until that number exceeds N, wherein computer processing comprises:
repetitively raising the first threshold by an incremental step S until the number of false positives that meet the criteria of calcium lesions counted no longer exceeds N;
repetitively lowering the first threshold by an incremental step size s, which is smaller than S, until the number of false positives that meet the criteria of calcium lesions exceeds N; and
repetitively raising the first threshold by a step z until the number of false positives counted no longer exceeds N,
wherein the signal threshold for the slice image is set substantially close to the value of the signal threshold value where the criteria of the calcium lesion counted no longer exceeds the value N.

37. The method of claim 36 wherein the region of interest is placed by the operator over a substantially homogeneous area in the slice image.

38. The method of claim 36 wherein the criteria further comprises at least one of a minimum connectedness and/or a minimum area.

39. The method of claim 38 wherein the region of interest is examined with a first threshold and the number of false positives that meet the criteria of calcium lesions is counted, wherein if the first threshold results in a number of false positives that is lower than or equal to the value N, computer processing comprises:
repetitively lowering the threshold by steps of 1 HU until the number of false positives that meet the criteria of calcium lesions counted is at N or exceeds the value N; and
setting the threshold substantially at the signal threshold value when the number of lesions is at or below N.

40. The method of claim 36 wherein the step S is between approximately 25 HU to 50 HU, step s is between approximately 10 HU and 25 HU, and step z is between approximately 1 and 10 HU.

41. The method of claim 36 where the step z is 1 HU.

42. The method of claim 36 where the step z is between 2 HU and 10 HU.

43. The method of claim 36 wherein substantially close is a value one HU step z below a signal threshold where the number of located false positives becomes N or smaller.

44. The method of claim 36 wherein the region of interest is examined with a first threshold and a number of false positives that meet the criteria of calcium lesions is counted, wherein if the first threshold results in a number of areas that are at or below N, computer processing comprises:
repetitively lowering the first threshold by an incremental step S until the number of false positives counted exceeds the value N;
repetitively raising the threshold by an incremental step size s, which is smaller than S, until the number of false positives is below the value N,
wherein the signal threshold for the slice image is set substantially close to the value of the signal threshold value where the false positives counted no longer exceeds N.

45. The method of claim 44 wherein the step s is between approximately 1 HU and 10 HU.

46. The method of claim 44 wherein the step s is between approximately 10 HU and 25 HU.

47. The method of claim 36 wherein the region of interest is examined with a first threshold and the number of false positives that meet the criteria of calcium lesions is counted until the number of false positives exceeds a value N; and,
repetitively raising the threshold by steps of 1 HU until the number of false positives counted no longer exceeds the value N; and
setting the signal threshold for the slice image substantially close to the value of signal threshold where the number of counted false positives is at or below N.

48. The method of claim 36 wherein computer processing comprises:
applying a first signal threshold $HU_1$ to the region of interest; and
counting the number of false positives located in the region of interest,
wherein if the number of false positives exceeds N, the method comprises:
repetitively raising the first signal threshold by steps S until the number of false positives becomes N or smaller and storing the raised signal threshold $HU_S$;
returning to the HU value of the threshold just prior to the one where $HU_s$ was reached;
repetitively raising the first signal threshold by steps s, that is smaller than steps S, until the number of false positives becomes N or smaller and storing the raised signal threshold $HU_s$;
returning to the HU value of the threshold just prior to the one where $HU_s$; was reached;
repetitively raising the first signal threshold a steps z that is smaller than steps s, until the number of false positives becomes N or smaller and storing the raised signal threshold $HU_z$; and
setting the threshold at a signal level that is substantially the one where the number of located false positives becomes N.

49. The method of claim 48 where step S is between approximately 25 HU to 50 HU, step s is between approximately 10 HU and 25 HU, and step z is 1 HU.

50. The method of claim 48 where step S is between approximately 25 HU to 50 HU, step s is between approximately 10 HU and 25 HU, and step z is between 2 and 10 HU.

51. The method of claim 48 where substantially close is a value one step z below the value where the number of located false positives becomes N.

52. The method of claim 36 wherein computer processing comprises:
applying a first signal threshold $HU_1$ to the region of interest;
counting the number of false positives located in the region of interest;
wherein if the number of false positives is less than N the method comprises:
repetitively lowering the first signal threshold by steps S until the number of false positives becomes N or larger and storing the raised signal threshold $HU_S$;
returning to the HU value of the threshold just prior to the one where $HU_S$ was reached;
repetitively lowering the first signal threshold by steps s, that is smaller than steps S, until the number of false positives becomes N or larger and storing the raised signal threshold $HU_s$;
returning to the HU value of the threshold just prior to the one where $HU_s$; was reached;
repetitively lowering the first signal threshold by steps z that is smaller than steps s, until the number of false positives becomes N or larger and storing the raised signal threshold $HU_z$; and
setting the threshold at a signal level that is substantially the one where the number of located false positives becomes N.

53. The method of claim 52 where step S is between approximately 25 HU to 50 HU, step s is between approximately 10 HU and 25 HU, and step z is 1 HU.

54. The method of claim 52 where step S is between approximately 25 HU to 50 HU, step s is between approximately 10 HU and 25 HU, and step z is between 2 and 10 HU.

55. The method of claim 52 where substantially close is a value one step z below the value where the number of located false positives becomes N.

56. A method of generating a signal threshold for each slice image of an image scan, the method comprising:
selecting a slice image from among a plurality of slice images comprising the image scan;
selecting at least one region of interest in the selected slice image;
generating a signal threshold for the selected slice image by applying an automatic search algorithm to the selected region of interest comprising steps of:
applying a first signal threshold $HU_1$ to the first region of interest; counting the number of false positives located in the region of interest that are located with the first signal threshold $HU_1$; comparing the number of counted false positives with the value of N; and performing at least one of lowering or raising the first signal threshold $HU_1$ until a signal threshold is found that generates N false positives or lower, wherein the individualized signal threshold for the slice image is et substantially closes to an adjusted signal threshold in with N false positives are found; and
selecting lesion criteria, wherein the lesion criteria comprises a minimum area of the lesion, a minimum connectedness of the lesion, and a number N of acceptable false positives in the region of interest, wherein the signal threshold is generated based on the lesion criteria; and
applying the signal threshold to the plurality of slice images to identify calcium in the slice images.

57. The method of claim 56 wherein the selected slice image is a slice image near a middle of the plurality of slice images.

58. The method of claim 56 wherein the selected slice image is one of a highest slice image from the plurality of slice images, a lowest slice image from the plurality of slice images, or a median slice image from the plurality of slice images.

* * * * *